(12) United States Patent
Colling

(10) Patent No.: US 10,056,162 B1
(45) Date of Patent: Aug. 21, 2018

(54) X-RAY SHIELDING SYSTEM FOR USE WITH AN X-RAY PRODUCING GANTRY

(71) Applicant: GLOBAL IMAGING SOLUTIONS COMPANY, Livonia, MI (US)

(72) Inventor: Timothy P. Colling, Farmington Hills, MI (US)

(73) Assignee: GLOBAL IMAGING SOLUTIONS COMPANY, Livonia, MI (US)

( * ) Notice: Subject to any disclaimer, the term of this patent is extended or adjusted under 35 U.S.C. 154(b) by 0 days.

(21) Appl. No.: 15/834,782

(22) Filed: Dec. 7, 2017

Related U.S. Application Data

(63) Continuation-in-part of application No. 15/710,649, filed on Sep. 20, 2017, which is a continuation-in-part of application No. 15/617,509, filed on Jun. 8, 2017, now Pat. No. 9,877,688, which is a continuation-in-part of application No. 15/427,414, filed on Feb. 8, 2017, now Pat. No. 9,867,583.

(51) Int. Cl.
  *A61B 6/00* (2006.01)
  *G21F 3/00* (2006.01)
  *A61B 6/10* (2006.01)

(52) U.S. Cl.
  CPC ............... *G21F 3/00* (2013.01); *A61B 6/107* (2013.01)

(58) Field of Classification Search
  CPC .......... A61B 6/107; A61B 6/0407; G21F 3/00
  USPC ...................... 250/505.1, 515.1, 517.1, 519.1
  See application file for complete search history.

(56) References Cited

U.S. PATENT DOCUMENTS

| | | | |
|---|---|---|---|
| 5,099,135 A | | 3/1992 | Gemmill |
| 5,417,225 A | * | 5/1995 | Rubenstein ............ A61B 90/04 128/849 |
| 5,981,964 A | * | 11/1999 | McAuley ................. G21F 3/00 250/515.1 |
| 6,448,571 B1 | | 9/2002 | Goldstein |
| 6,653,648 B2 | | 11/2003 | Goldstein |
| 6,703,632 B1 | | 3/2004 | Macklis et al. |
| 9,177,681 B2 | | 11/2015 | Morris |
| 9,451,922 B2 | | 9/2016 | Buchmeyer |
| 2012/0148335 A1 | | 6/2012 | Nourry et al. |

FOREIGN PATENT DOCUMENTS

| | | |
|---|---|---|
| CN | 201127616 | 10/2008 |
| DE | 2614202 | 10/1977 |

\* cited by examiner

*Primary Examiner* — Michael Maskell
(74) *Attorney, Agent, or Firm* — Brooks Kushman P.C.

(57) ABSTRACT

Disclosed is a shielding system for customized shielding of a patient or an operator from X-rays generated from a gantry. The shielding system is mounted on the gantry. The system has a rail that is arcuately movable in relation to gantry-mounted foundational blocks with apertures that receive a proximal section of the rail. Protective curtains are suspended from intermediate and/or distal sections of the rail.

20 Claims, 3 Drawing Sheets

X-RAY SHIELDING SYSTEM FOR USE WITH AN X-RAY PRODUCING GANTRY

CROSS-REFERENCE TO RELATED APPLICATIONS

This application claims the benefit of and is a continuation-in-part of U.S. Ser. No. 15/710,649 filed Sep. 20, 2017 which claims the benefit of and is a continuation-in-part of U.S. Ser. No. 15/617,509 filed Jun. 8, 2017, now U.S. Pat. No. 9,877,688 issued Jan. 30, 2018, which claims the benefit of and is a continuation-in-part of U.S. Ser. No. 15/427,414, now U.S. Pat. No. 9,867,583 issued Jan. 16, 2018 which was filed on Feb. 8, 2017, the disclosures of which are incorporated herein in their entirety.

TECHNICAL FIELD

This disclosure includes a customizable x-ray shielding system for primary use with an X-ray producing gantry.

BACKGROUND

As used herein, the term "gantry" includes the 'donut' shaped part of a CT scanner that houses the components necessary to produce and detect x-rays to create a CT image. Typically, the x-ray tube and detectors are positioned opposite each other and rotate around the gantry aperture. In some settings, a patient lies on a table such that there is relative movement between the table and the gantry.

Among the art considered in preparing this patent application are these references: U.S. Pat. Nos. 5,099,135; 5,417,225; 6,448,571; and 6,653,648.

SUMMARY

Disclosed is a shielding system for customized protection from X-rays. The shielding system is mounted on an x-ray producing gantry. The gantry, if desired, can be tilted so that it may lie in a plane that is about, for example, plus or minus 45 degrees from a vertical plane.

In use over the various orientations of such machines there is a need to isolate the technician or physician from X-radiation. To do this, shielding devices such as lead or other radio-opaque curtains are often used. Such curtains can be suspended from a movable, adjustable rail system so that their placement is predictable, yet adjustable regardless of machine orientation.

One way to achieve the goal of reliably supporting such shielding devices is to suspend them from a rail system that is mounted in a foundational block which is affixed preferably to an upright or other face of the movable gantry. Optionally the block can be secured to a gantry-mounted track that enables the block's position to be further adjusted. If desired, multiple foundational blocks may be affixed to the gantry.

Facing an upright, usually vertical plane of the gantry is a back surface (A) of each foundational block. A rail-receiving aperture extends between the top surface (C) and an opposing bottom surface (D). Each aperture is configured to receive a proximal end region of an arcuately movable rail from which, for example, a radio-opaque curtain can be suspended if desired under the influence of gravity in a vertical plane. One or more detents are defined by the top surface (C). At least some of the detents are configured to be in registration with one or more lugs that extend radially from a proximal end region of the bracket. Upon registration, there is little or no twisting movement of the rail in relation to the foundational block.

The rail has a proximal section that is seated in an aperture. Extending from the proximal section of the rail is an optional intermediate section that terminates in a distal section. If the intermediate section is absent, the distal section extends from the proximal section. In use, a rail can be turned within an associated aperture. Regardless of gantry orientation, one or more radio-opaque curtains can be suspended from a given rail in a desired position by positioning the rail in the aperture, thereby rotating it in relation to the associated aperture and then seating one or more lugs in a suitable detent.

The intermediate rail section extends from the proximal section, preferably orthogonally thereto, but not necessarily so. For example, the angle between theses sections may lie between 60 and 120 degrees. Between these two sections there is a first transition region, which may define a right angle or be curved.

Extending from the intermediate section is the distal section, which in turn is preferably orthogonally to the intermediate section, but not necessarily so. The term "orthogonally" as used herein means generally at right-angles. In the first transition region (between the proximal and intermediate sections) there may be a relatively abrupt transition (e.g., a right angle), or the first transition region may be curved.

A second transition region may lie between the intermediate and distal sections. Like the first transition region, the second transition region may be oriented such that the intermediate section is not coplanar with the distal section.

The optional intermediate section may be desirable in such cases as patient head examinations. There, the patient may be more relaxed due to additional spacing from the radio opaque curtain that is provided by the intermediate and distal sections of the rail. Another advantage of such a rail is the additional spacing between the patient and an x-ray impervious curtain thereby provided during an interventional exam.

It will be appreciated that a curtain may be suspended from a distal section, an intermediate section or be draped therebetween.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Disclosed is a shielding system 10 for use in alternative configurations as user-selected, customized shielding from X-rays. The shielding system 10 is mounted on a foundational block 26 that is attached to a gantry 12. In use, the usually near-vertical plane of the gantry 12 can be tilted if desired through an angular range of about 45 degrees from a vertical plane.

Figure 1:
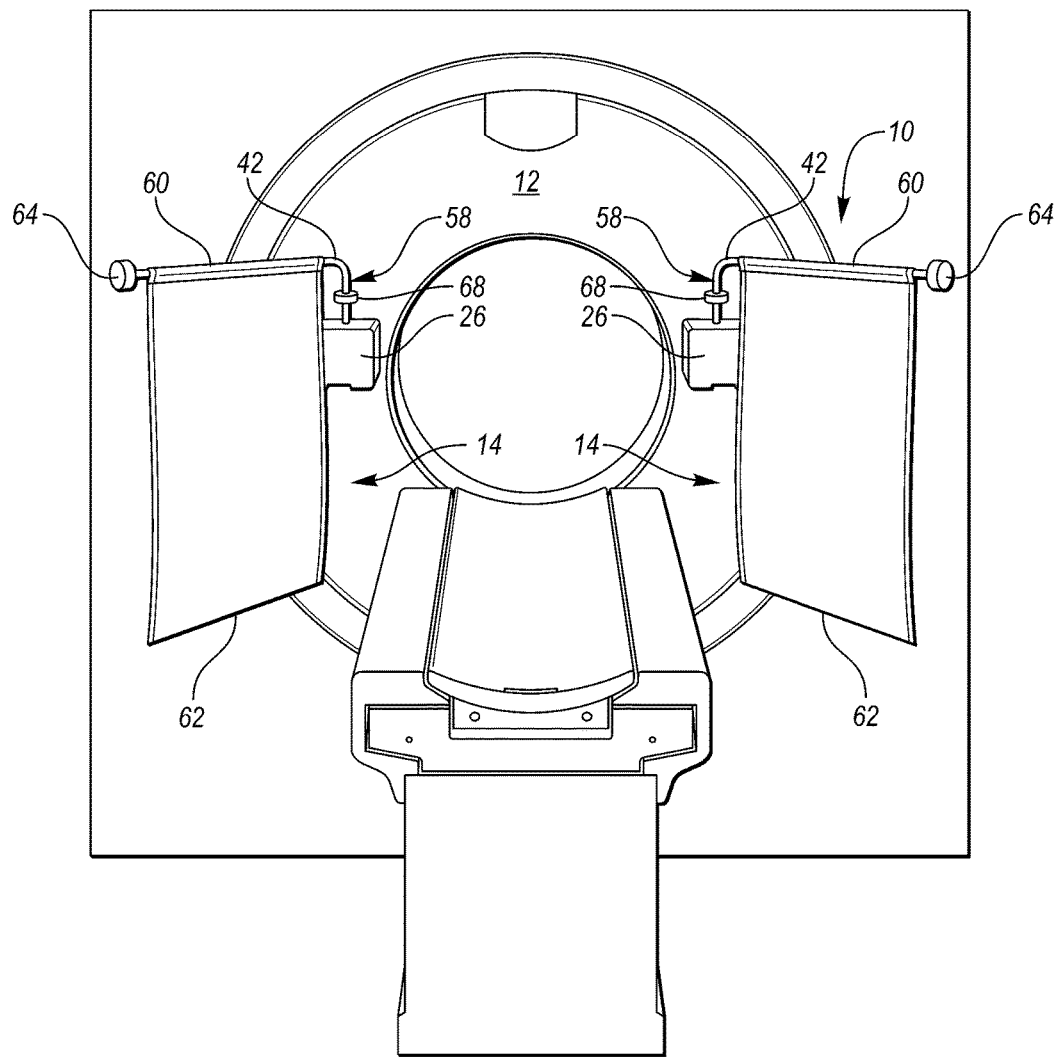
FIG. 1 is a quartering perspective view of a typical environment in which a shielding system is deployed, including a rail from which a lead curtain is suspended.

In the shielding system 10 associated with a given gantry 12, there are one or more foundational blocks 26 (see, e.g. FIG. 1).

Figure 2:
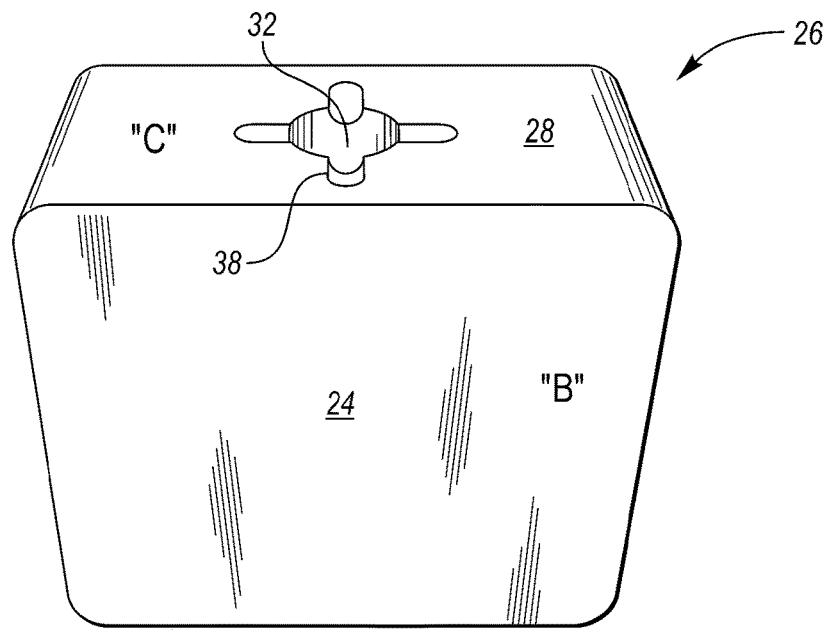
FIG. 2 depicts a representative top surface (C) with detents that receive lugs extending from a proximal end region of the rail and front surface (B) of a foundational block that form a part of the shielding system.
Figure 3:
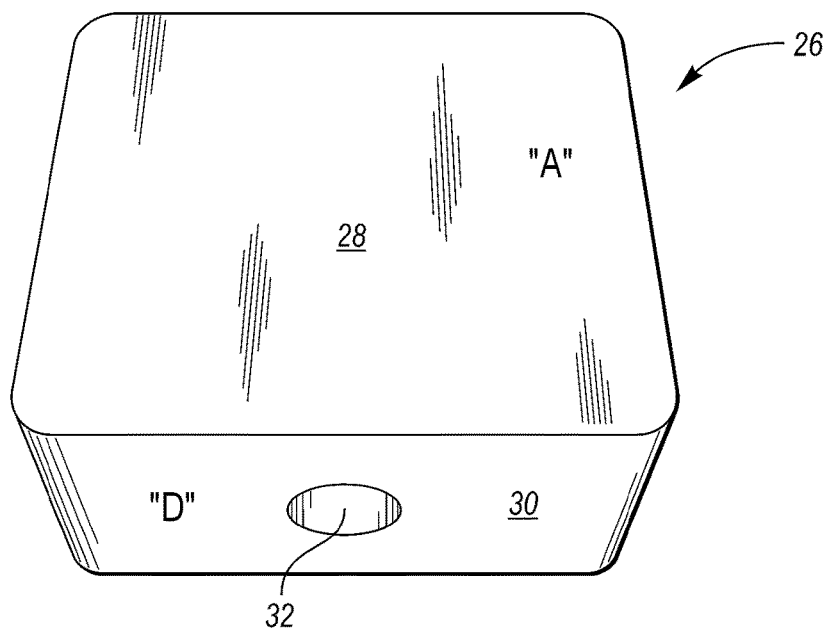
FIG. 3 depicts a representative bottom surface (D) and back gantry-facing surface (A) of the foundational block.

Facing the block-mounting surfaces 14 of the gantry 12 is a back surface (A) 28 of the foundational block (FIG. 3). A post-receiving aperture 32 extends between the top surface (C) 28 (FIG. 2) and an opposing bottom surface (D) 30 (FIG. 3). One or more detents 38 are defined within the top surface (C). Each detent 38 is configured to be in registration with a lug or pin that extends generally radially from a proximal section 58 of the rail 42. Upon registration of the rail 42 within an associated detent 38, there is little or no twisting movement of the rail 42 in relation to the foundational block 26.

One or more apertures 32 extend between the bottom surface (D) 30 and the opposing top surface (C) 28. Each major aperture is configured to receive a rail 42.

Figure 4:
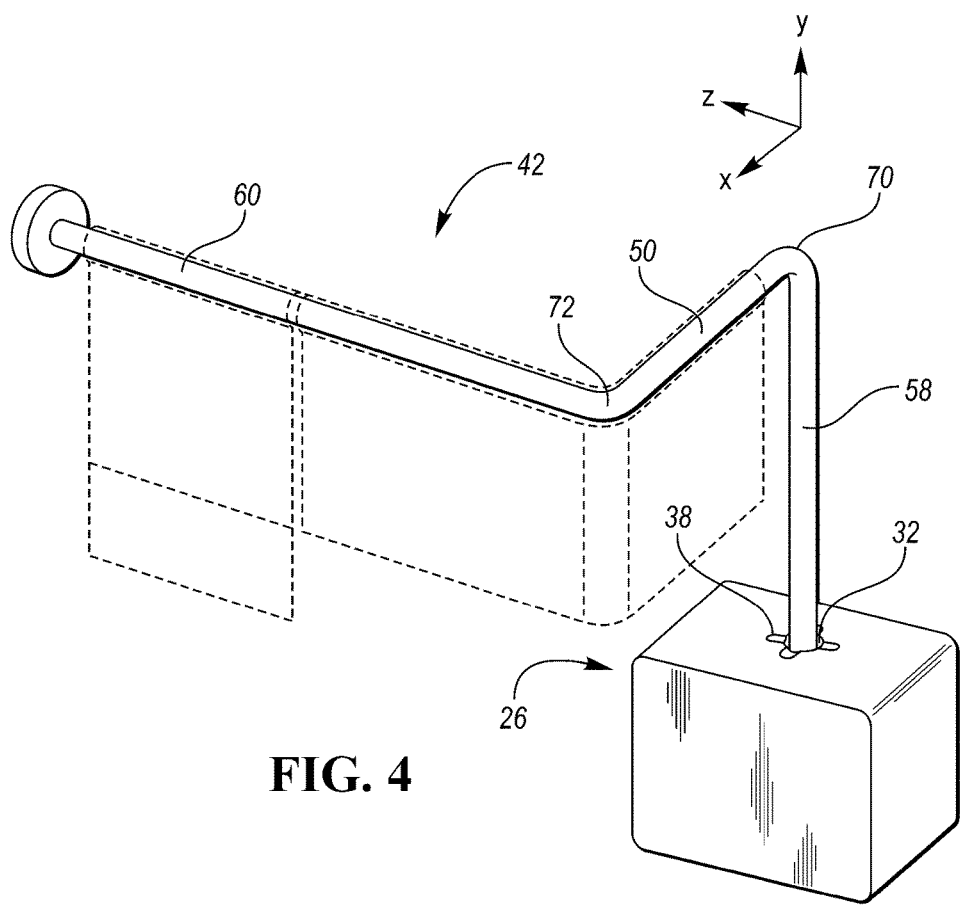
FIG. 4 illustrates a rail with an optional intermediate section.

Each rail 42 has a proximal section 58 (FIGS. 1, 4) that is received by a major aperture 32 of a foundational block 26. Extending from the proximal section 58 is an optional intermediate section 50 (FIG. 4) and a distal section 60. It will be appreciated that the distal section 60 need not be orthogonal with the intermediate section 50, and that the intermediate section 50 need not be orthogonal with the proximal section 58. Other angular relationships between about 30 and 90 degrees may be desirable, depending on the installation. Further, the distal section 60 need not be co-planar with the intermediate section 50, and the intermediate section 50 need not be co-planar with the proximal section 58. In such cases a first and second transition region between the respective sections may be curved.

Suitable materials from which a rail system may be made include stainless steel and composites. In practice, the intermediate section 50 and/or the distal section 60 may be formed so that they have a slightly upward tilt. In this way, under the added weight of a lead curtain, these sections may bend downwardly toward a generally horizontal orientation, thereby resisting slippage of the curtain(s).

Regardless of gantry orientation, one or more radio-opaque curtains 62 can be hung from the distal section 60 and/or the intermediate section 50 to allow flexibility in adapting to operator and patient examination requirements. It will be appreciated that the curtains 62 are preferably formed from an x-ray absorbing material. Such curtains 62 may for example be 20" long×26" wide. But the curtains 62 can be of any length and width. Further, the curtains 62 may have any desired x-ray attenuation characteristics.

The intermediate section 50 of the rail system 42 may be desirable for many applications. Such a section allows for the opaque curtain to be positioned further away from any sterile field. Further the patient may be more comfortable because the risk of claustrophobia is reduced.

In one embodiment, there is a knob 64 that is received at an end of the distal section 60 of the rail 42 for constraining lateral movement of the one or more radio-opaque curtains 62 along the distal section 60 of the rail 42.

Preferably the apertures 32 terminate at the opposing top surface (C) 28 (FIG. 2) and slots 38 extend radially from the apertures 32. The slots 32 are configured to engage lugs 68 that extend radially from the proximal section 58 of the rail 42 to preclude a twisting motion of the rail 42 when seated within an associated aperture 32. This feature influences rail positioning regardless of gantry orientation.

In most uses, a rail 42 can be twisted within an associated major aperture 32 so that the distal section 60 of the rail 42 can be made to extend substantially horizontally regardless of gantry orientation.

Optionally, the rail position is secured by engaging a lug 68 within a slot 38. It will be appreciated that the distal section 60 of the rail 42 may be arcuately positioned so that the distal section 60 extends horizontally. Optionally, if desired, the distal section 60 may lie in parallel with a face of the gantry.

In some cases, each gantry has one or two foundational blocks 26 for optimized shielding of the patient and operator from radiation. Each block 26 supports a rail 42. Preferably there are up to four blocks 26 per gantry. Placement of the block 26 is not restricted to a front face of the gantry. The patient table protrudes through the gantry (donut hole). This allows for the patient's anatomy to be positioned adjacent to the gantry's front facing side and the back facing side. It will be appreciated that the foundational blocks 26 could be and are likely to be attached to either or both sides of the gantry 12 to promote shielding of the technician, physician or patient. Further, foundational blocks 26 may be positioned not only on either gantry face but also on the sides, top or any other suitable location on the gantry 12.

To secure a foundational block 26 in relation to the gantry 12, means for securement are provided. Such securement means include, for example, a threaded bolt, a screw, a rivet, cement or a glue.

In some cases, the gantry orientation lies between plus and minus 45 degrees from a vertical plane.

Although the foundation blocks 26 are depicted as generally brick-shaped, it will be appreciated that such blocks may be shaped in various geometries and sizes, and have non-parallel faces that may or may not be planar. For example, some of the faces of the foundational block may be curved in such a way as to avoid sharp corners or edges.

TABLE OF REFERENCE NUMERALS

10 shielding system
12 gantry
14 foundational block optional mounting placements
25 front surface (B)
26 foundational blocks
28 back (gantry-facing) surface (A)
30 bottom surface (D)
32 rail-receiving aperture
38 detent
42 rail
50 intermediate section of rail
58 proximal section of rail
60 distal section of rail
62 radio-opaque curtain
64 knob
68 lugs
70 first transition region
72 second transition region While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. An x-ray shielding system for customized shielding from x-rays generated from a gantry, the shielding system comprising:
    one or more foundational blocks, each block having one or more rail-receiving apertures that extend at least partially from a top surface;
    a detent defined by the top surface, the detent being configured to be in registration with a lug that extends radially from a proximal section of a rail so that upon registration, there is little or no movement of the rail in relation to the foundational block;
    the rail having an intermediate section extending from the proximal section; and
    a distal section extending from the intermediate section so that one or more radio-opaque curtains can be suspended from the intermediate and/or distal sections.

2. The shielding system of claim 1, further including:
    a knob that is received at an end of the distal section of the rail for constraining lateral movement of the one or more radio-opaque curtains along the distal section of the rail.

3. The shielding system of claim 1, wherein one of the one or more rail-receiving apertures terminates at the top surface and the detents extend radially from the post-receiving aperture, the detents being configured to engage lugs that extend radially from the proximal section of the rail to preclude a twisting motion of the rail within an associated aperture when the proximal section is seated, thereby influencing rail positioning regardless of gantry orientation.

4. The shielding system of claim 1, wherein one rail orientation is such that the intermediate and/or the distal section extends generally horizontally.

5. The shielding system of claim 1, wherein the intermediate section extends forwardly away from the gantry.

6. The shielding system of claim 1, wherein the rail can be twisted within an aperture so that the distal section of the rail extends horizontally regardless of gantry orientation.

7. The shielding system of claim 1 wherein there are more than one intermediate sections.

8. The shielding system of claim 1, wherein there are two or more foundational blocks attached to a face of the gantry, each supporting one or more rails, at least one rail having one or more intermediate sections and a distal section extending horizontally, and another rail having a distal section that lies in another orientation.

9. The shielding system of claim 1, wherein the foundational block has faces that are non-parallel and that may or may not be planar.

10. The shielding system of claim 1, wherein the gantry has a front face, a back face and side edges and the one or more foundational blocks are attached to one or more of such faces.

11. The shielding system of claim 1, wherein the distal section lies at an angle other than 90 degrees from the intermediate section.

12. The shielding system of claim 1, wherein the intermediate section lies at an angle other than 90 degrees from the proximal section.

13. The shielding system of claim 1, wherein the distal section lies at an angle between about 30 and 90 degrees from the intermediate section.

14. The shielding system of claim 1, wherein the intermediate section lies at an angle between about 30 and 90 degrees from the proximal section.

15. The shielding system of claim 1, wherein the distal section lies at an intermediate position between the X-X and Y-Y axes.

16. The shielding system of claim 1, wherein a foundational block has non-parallel faces that may or may not be planar.

17. The shielding system of claim 1, further including a first transition region between the proximal and intermediate sections, the first transition region being a relatively abrupt transition or curved.

18. The shielding system of claim 1, further including a second transition region between the intermediate and distal sections, the second transition region being a relatively abrupt transition or curved.

19. The shielding system of claim 17, wherein the first transition region is such that the intermediate section is not co-planar with the proximal section.

20. The shielding system of claim 18, wherein the second transition region is such that the intermediate section is not co-planar with the distal section.

* * * * *